(12) United States Patent
Knodel

(10) Patent No.: US 8,261,958 B1
(45) Date of Patent: Sep. 11, 2012

(54) STAPLER CARTRIDGE WITH STAPLES FRANGIBLY AFFIXED THERETO

(75) Inventor: Bryan D. Knodel, Flagstaff, AZ (US)

(73) Assignee: Cardica, Inc., Redwood City, CA (US)

( * ) Notice: Subject to any disclaimer, the term of this patent is extended or adjusted under 35 U.S.C. 154(b) by 0 days.

(21) Appl. No.: 12/683,382

(22) Filed: Jan. 6, 2010

(51) Int. Cl.
*A61B 17/072* (2006.01)

(52) U.S. Cl. ..................... 227/176.1; 227/19

(58) Field of Classification Search .... 227/175.1–182.1, 227/19, 901, 902; 606/219
See application file for complete search history.

(56) References Cited

U.S. PATENT DOCUMENTS

| | | | |
|---|---|---|---|
| 3,581,551 A | 6/1971 | Wilkinson | |
| 3,650,453 A | 3/1972 | Smith, Jr. | |
| 3,899,914 A | 8/1975 | Akiyama | |
| 4,086,926 A | 5/1978 | Green et al. | |
| 4,228,895 A | 10/1980 | Larkin | |
| 4,475,679 A | 10/1984 | Fleury, Jr. | |
| 4,589,416 A | 5/1986 | Green | |
| 4,633,861 A | 1/1987 | Chow et al. | |
| 4,762,260 A | 8/1988 | William et al. | |
| 4,969,591 A * | 11/1990 | Richards et al. | 227/177.1 |
| 5,156,315 A | 10/1992 | Green et al. | |
| 5,192,288 A | 3/1993 | Thompson et al. | |
| 5,413,272 A | 5/1995 | Green et al. | |
| 5,476,206 A | 12/1995 | Green | |
| 5,655,698 A | 8/1997 | Yoon | |
| 5,662,260 A | 9/1997 | Yoon | |
| 5,692,668 A | 12/1997 | Schulze et al. | |
| 5,810,855 A | 9/1998 | Rayburn et al. | |
| 5,816,471 A | 10/1998 | Plyley et al. | |
| 5,855,311 A | 1/1999 | Hamblin et al. | |
| 5,894,979 A | 4/1999 | Powell | |
| 5,918,791 A | 7/1999 | Sorrentino et al. | |
| 5,964,774 A | 10/1999 | McKean et al. | |
| 6,306,149 B1 | 10/2001 | Meade | |
| 6,391,038 B2 | 5/2002 | Vargas et al. | |
| 6,602,252 B2 | 8/2003 | Mollenauer | |
| 6,716,232 B1 | 4/2004 | Vidal et al. | |
| 6,817,508 B1 | 11/2004 | Racenet | |
| 6,843,403 B2 | 1/2005 | Whitman | |
| 7,025,747 B2 | 4/2006 | Smith | |
| 7,055,730 B2 | 6/2006 | Ehrenfels et al. | |

(Continued)

FOREIGN PATENT DOCUMENTS

EP    1238634    9/1994

(Continued)

OTHER PUBLICATIONS

Gong, Shao W., "Perfectly flexible mechanism and integrated mechanism system design", *Mechanism and Machine Theory 39* (2004), (Nov. 2004),1155-1174.

(Continued)

*Primary Examiner* — Lindsay Low
*Assistant Examiner* — Andrew M Tecco

(57) ABSTRACT

A surgical apparatus may include a cartridge, and surgical staples affixed to and frangibly separable from that cartridge. A method for surgical stapling utilizing that apparatus may include providing at least one wedge; and moving at least one wedge into the cartridge, where that moving deforms and then shears from the cartridge at least one staple. A method of manufacturing an apparatus for use with a surgical stapler may include fabricating a cartridge configured to be received by the surgical stapler; fabricating staples; and fixing the staples to the cartridge.

11 Claims, 4 Drawing Sheets

U.S. PATENT DOCUMENTS

| | | | |
|---|---|---|---|
| 7,097,089 | B2 | 8/2006 | Marczyk |
| 7,140,527 | B2 | 11/2006 | Ehrenfels et al. |
| 7,168,604 | B2 | 1/2007 | Milliman et al. |
| 7,172,104 | B2 | 2/2007 | Scirica et al. |
| 7,179,267 | B2 | 2/2007 | Nolan et al. |
| 7,207,471 | B2 | 4/2007 | Heinrich et al. |
| 7,213,736 | B2 | 5/2007 | Wales et al. |
| 7,225,963 | B2 | 6/2007 | Scirica |
| 7,225,964 | B2 | 6/2007 | Mastri et al. |
| 7,234,624 | B2 | 6/2007 | Gresham et al. |
| 7,238,195 | B2 | 7/2007 | Viola |
| 2003/0120284 | A1 | 6/2003 | Palacios et al. |
| 2003/0236551 | A1 | 12/2003 | Peterson |
| 2005/0184121 | A1 | 8/2005 | Heinrich |
| 2006/0011699 | A1 | 1/2006 | Olson et al. |
| 2006/0041273 | A1 | 2/2006 | Ortiz et al. |
| 2006/0151567 | A1 | 7/2006 | Roy |
| 2007/0027472 | A1 | 2/2007 | Hiles et al. |
| 2007/0034668 | A1 | 2/2007 | Holsten et al. |
| 2007/0073341 | A1 | 3/2007 | Smith et al. |
| 2007/0083234 | A1 | 4/2007 | Shelton, IV et al. |
| 2007/0118163 | A1 | 5/2007 | Boudreaux et al. |
| 2007/0119902 | A1* | 5/2007 | Vargas et al. ............. 227/180.1 |
| 2007/0125828 | A1 | 6/2007 | Rethy et al. |
| 2007/0175950 | A1 | 8/2007 | Shelton, IV et al. |
| 2008/0078807 | A1* | 4/2008 | Hess et al. ................. 227/181.1 |
| 2008/0210738 | A1* | 9/2008 | Shelton et al. ............. 227/176.1 |
| 2008/0312687 | A1* | 12/2008 | Blier ........................... 606/219 |
| 2009/0065552 | A1* | 3/2009 | Knodel et al. ............. 227/180.1 |

FOREIGN PATENT DOCUMENTS

| | | |
|---|---|---|
| EP | 1464287 | 10/2004 |
| EP | 1736104 | 3/2009 |
| JP | 2005160933 | 6/2005 |
| RU | 2080833 | 6/1997 |
| WO | WO-81/01953 | 7/1981 |
| WO | WO-85/01427 | 4/1985 |

OTHER PUBLICATIONS

Lim, Jonas J., et al., "A review of mechanism used in laparascopic surgical instruments", *Mechanism and Machine Theory 38*, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004),265-272.

Kolios, Efrossini et al., "Microlaparoscopy", *J. Endourology 18(9)*, (Nov. 2004),811-817.

Steichen, Felicien M., et al., "Mechanical Sutures in Surgery", *Brit. J. Surg. 60(3)*, (Mar. 1973),191-197.

"Notification of Transmittal of the International Search Report and the Written Opinion of the International Searching Authority", PCT/US2008/075449.

"International Search Report", PCT/US2008/075449.

"Written Opinion of the International Searching Authority", PCT/US2008/075449.

"Cardica Microcutter Implant Delivery Device 510(k), Cover Sheet, Table 10.1, "Substantial Equivalence Comparison," and Section 12, "Substantial Equivalence Discussion"", Oct. 18, 2010.

\* cited by examiner

STAPLER CARTRIDGE WITH STAPLES FRANGIBLY AFFIXED THERETO

FIELD OF THE INVENTION

The invention generally relates to surgical staplers and stapling.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. The staples may be held in individual pockets, with staple drivers underneath each staple. As a wedge advances into the cartridge, that wedge sequentially pushes a number of staple drivers upward, and the staple drivers in turn both linearly push each corresponding staple upward out of its pocket, deforming it against an anvil. The manufacturing process required to place those small individual staples and staple drivers in the corresponding small pockets is difficult, and the number of parts involved complicates the system and requires a minimum size of cartridge that may be larger than optimally desired.

BRIEF DESCRIPTION OF THE DRAWINGS

The use of the same reference symbols in different figures indicates similar or identical items.

DETAILED DESCRIPTION

U.S. patent application Ser. No. 12/400,790, filed on Mar. 9, 2009 (the "Feeder Belt Document"), is hereby incorporated by reference herein in its entirety. The Feeder Belt Document describes exemplary feeder belts used in a surgical stapler, to which a plurality of staples are frangibly connected. Because new staples are fed to an end effector of a surgical stapler by the feeder belts for sequential deployment, the surgical stapler of the Feeder Belt Document does not need or utilize a plurality of single-use cartridges in order to deploy multiple sets of staples.

Figure 1:
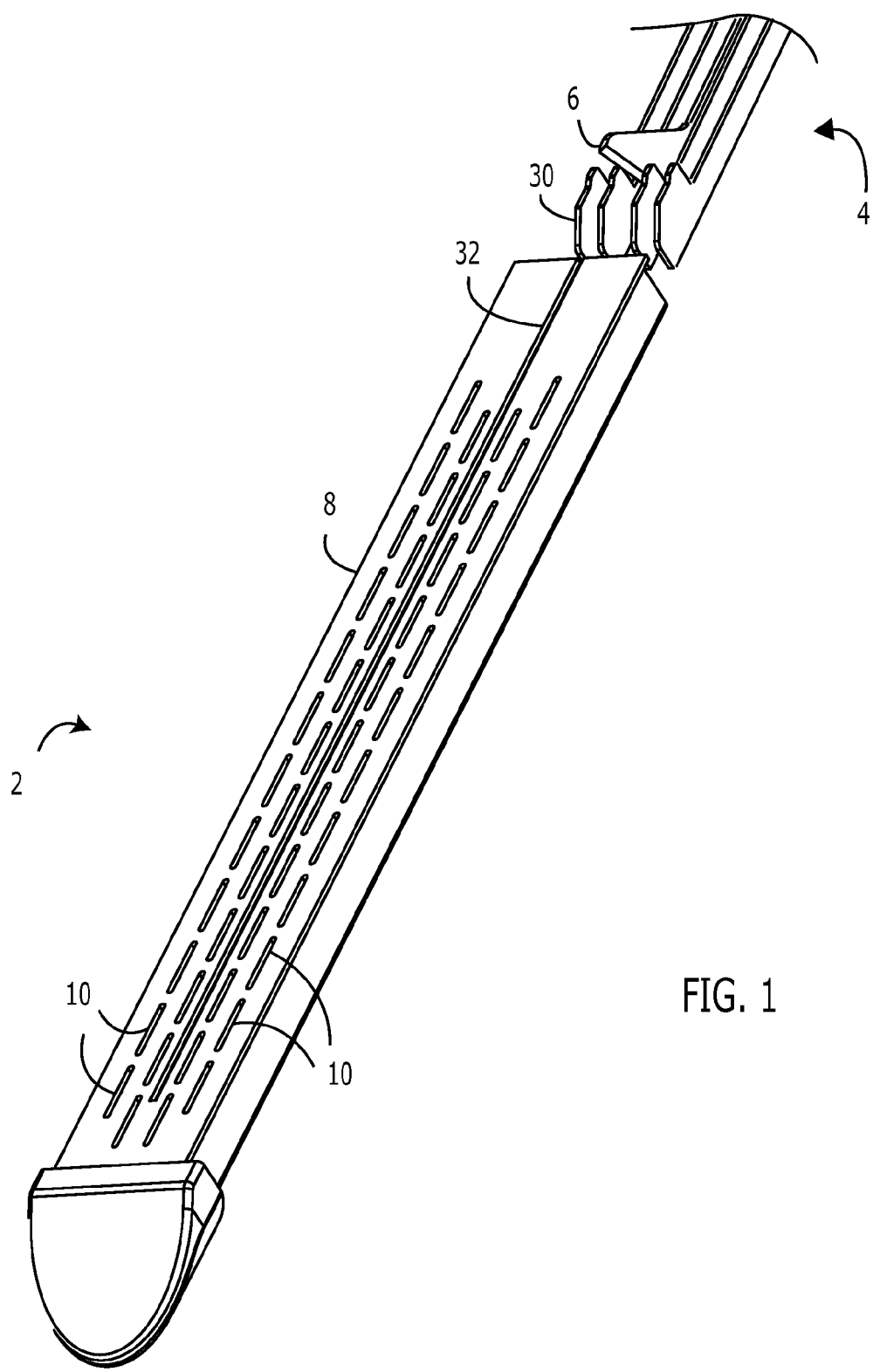
FIG. 1 is a perspective view of an exemplary cartridge and exemplary wedge assembly.

As is commonly used in the medical device industry, particularly in the surgical stapler business, the term "cartridge" means, and is expressly defined in this document to mean, a portion of a surgical stapler that holds at least one staple, and that is insertable within and releasably connected to a remainder of the surgical stapler. Referring to FIG. 1, an exemplary cartridge 2 is shown, along with an exemplary wedge assembly 4 and knife 6. The cartridge 2 may be utilized in conjunction with any surgical stapler that is capable of receiving it, and that includes at least a wedge assembly 4 capable of moving into the cartridge 2 to deploy staples (as described in greater detail below) and then moving out of the cartridge 2 to allow the spent cartridge 2 to be removed from the surgical stapler. The cartridge 2 may be received in a remainder of a surgical stapler in any suitable manner, such as by a pressure fit or interference fit; passively or affirmatively; or in any other suitable manner. The cartridge 2 may be received at the distal end of a remainder of the surgical stapler, and/or along the side of a remainder of the surgical stapler. The cartridge 2 may be useful in conjunction with an articulated surgical stapler having an articulation proximal to the location at which the cartridge is attached to the stapler. Such an articulation may be, for example, as described in U.S. patent application Ser. No. 12/400,760, filed on Mar. 9, 2009, or in U.S. patent application Ser. No. 12/612,614, filed on Nov. 4, 2009, both of which are hereby incorporated by reference in their entirety.

The cartridge 2 may be shaped in any suitable manner. As one example, the cartridge 2 may include an upper surface 8. The upper surface 8 may be generally flat, and generally rectangular. However, the upper surface 8 need not be generally flat along all or part of its area, and may be shaped in a manner other than rectangular. Further, the upper surface 8 need not be a discrete part of the cartridge 2, and instead simply may be a portion of a larger surface or area of the cartridge 2. The upper surface 8 of the cartridge 2 may include a plurality of openings 10 defined completely therethrough. As described in greater detail below, each opening 10 may be aligned with a corresponding staple, such that a staple may be deployed through each opening 10. Each opening 10 may be generally longitudinally-oriented, and generally rectangular in shape. Alternately, the orientation and/or shape of at least one opening 10 may be different. The openings 10 may be organized into one or more generally-longitudinally-oriented rows, corresponding to the locations of staples in the cartridge 2. As another example, the openings 10 may be interconnected to form one or more larger openings, such that more than one staple may be deployed through a single opening 10. Alternately, the upper surface 8 may be omitted altogether, thereby rendering openings 10 superfluous.

Figure 2:
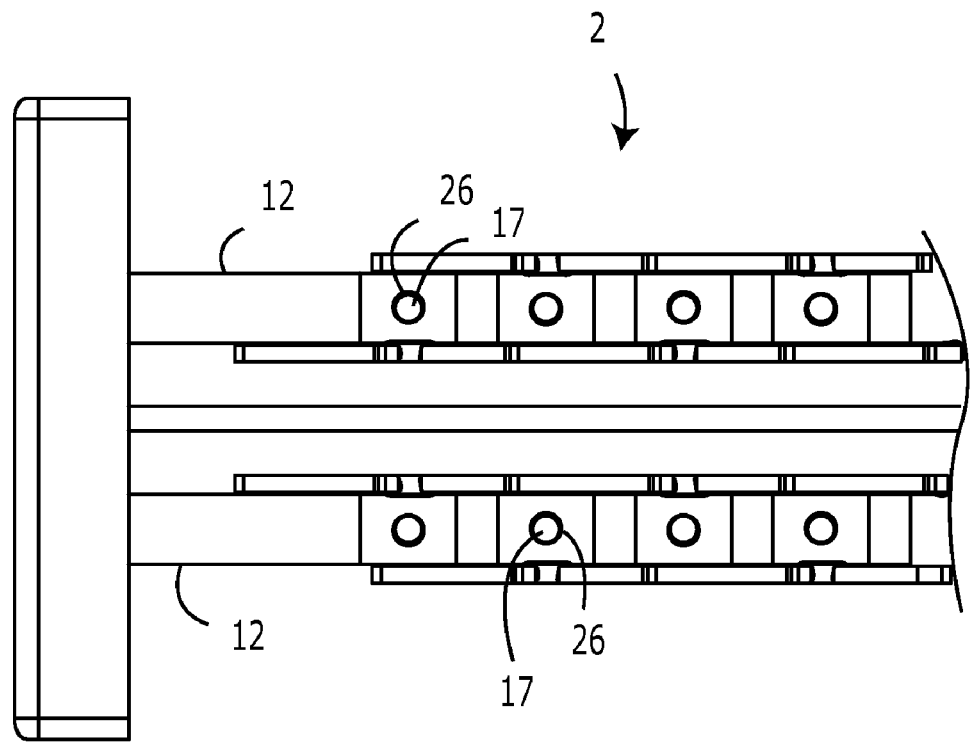
FIG. 2 is a top cutaway view of the exemplary cartridge of FIG. 1.
Figure 3:
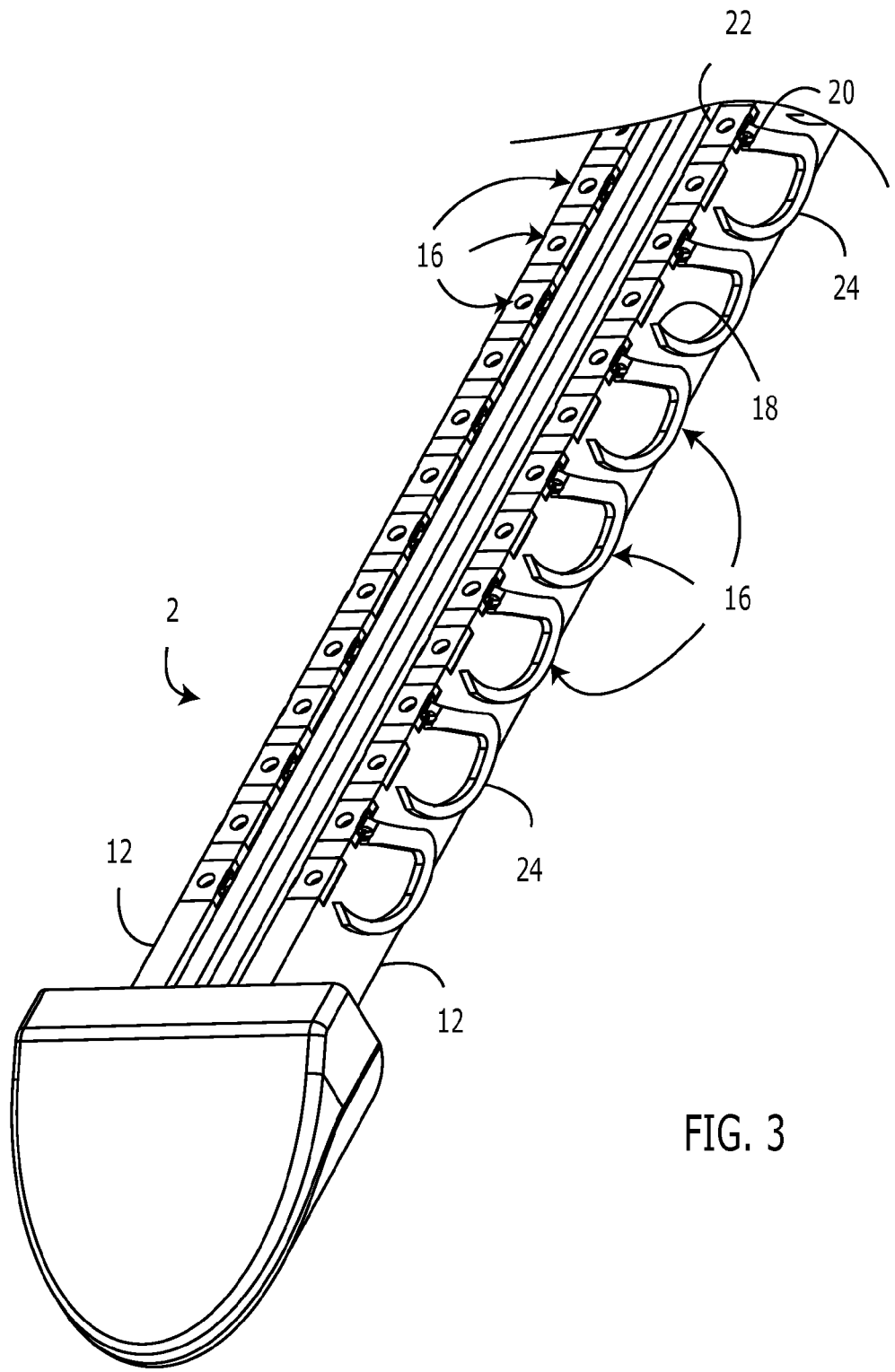
FIG. 3 is a perspective cutaway view of the exemplary cartridge of FIG. 1.
Figure 4:
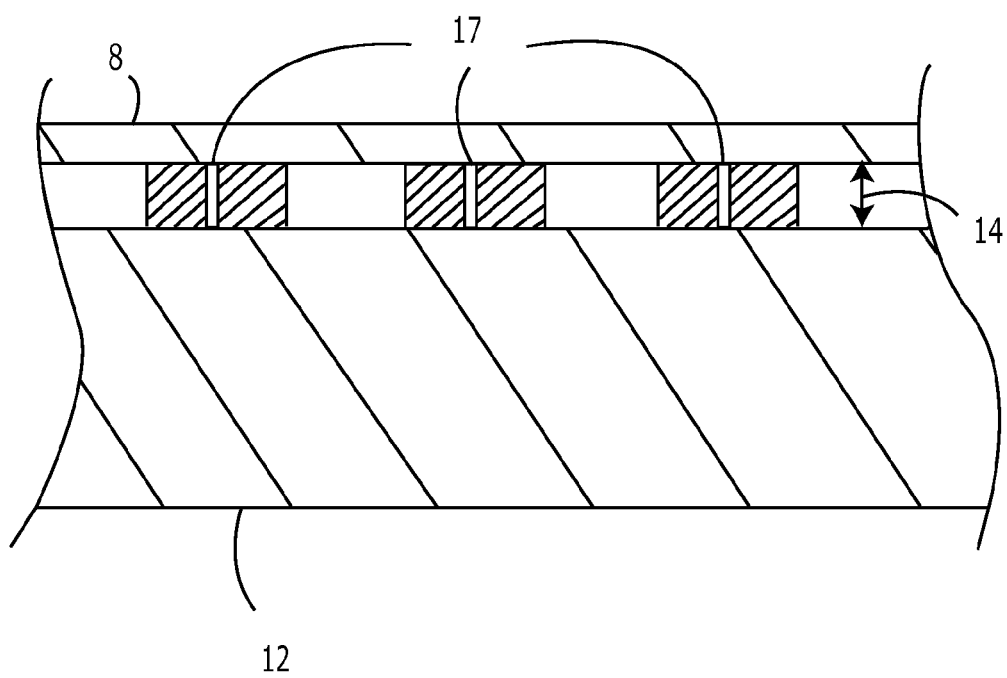
FIG. 4 is a side cross-section view of the exemplary cartridge of FIG. 1, with staples omitted for clarity.

Referring also to FIGS. 2-4, the cartridge 2 also may include one or more rails 12. The rails 12 may be oriented generally longitudinally, and may be shaped generally as rectangular solids. At least one rail 12 may be dimensioned greater in lateral width than in vertical height, as seen most clearly in FIG. 3. As another example, at least one rail 12 may be oriented and/or shaped in any other suitable manner. The rails 12 may be spaced laterally apart from one another. The rails 12 may be fabricated from any suitable material, and in any suitable manner. At least one rail 12 may be vertically spaced apart from the upper surface 8 of the cartridge 2 by a gap 14. One or more pins 17 may extend from at least one rail 12 across the gap 14 to the upper surface 8. The pins 17 may be fabricated integrally with the corresponding rail 12 and/or upper surface 8, or may be fabricated separately and later connected thereto. At least one pin 17 may be generally cylindrical in shape. However, at least one pin 17 may be shaped differently. The pins 17 advantageously are shaped the same as one another, but at least one pin 17 may be shaped differently than at least one other pin 17.

A plurality of staples 16 may be affixed to and frangibly separable from the cartridge 2. The staples 16 may be shaped substantially in the same manner as the staples described in the Feeder Belt Document, or may be shaped in any other suitable manner. Each staple 16 may have a free end 18, and an opposite end 20 that is connected to a stem 22. The portion of the staple 16 between the free end 18 and the opposite end 20 may be referred to as the tine 24. The stem 22 of at least one staple 16 may be substantially perpendicular to the tine 24 of that staple 16. As another example, the stem 22 and tine 24 of a staple 16 may be oriented at a different angle to one another. The stem 22 may be substantially planar and rectangular, but may be shaped differently if desired. Each tine 24 may be fixed to the corresponding stem 22. Advantageously, the tine 24 and corresponding stem 22 are integral, and may be fabricated by stamping a piece of flat sheet metal, then bending the tine 24 and the stem 22 to the desired angle relative to one another. Advantageously, each staple 16 is positioned on a corresponding rail 12, such that the stem 22 is positioned on top of that rail 12. The thickness of the stem 22 may be substantially the same as the height of the gap 14 between each rail 12 and the upper surface 8. Alternately, the thickness of at least one stem 22 may be less than the height of the gap 14 between each rail 12 and the upper surface 8. Each staple 16 may be fixed to the upper surface 8 of the cartridge and/or to a rail 12, in any suitable manner. As one example, at least one stem 22 may include at least one aperture 26 defined therethrough. That aperture 26 may receive a corresponding pin 17 that extends from the upper surface 8 to a rail 12. As another example, at least one stem 22 may be welded to the top of a corresponding rail 12 and/or to the bottom of the upper surface 8. As another example, at least one stem may be affixed to the top of a corresponding rail 12 and/or to the bottom of the upper surface 8 by adhesive. As another example, at least one stem 22 may be pressure-fit between the upper surface 8 and the corresponding rail 12. As another example, at least one stem 22 may be fixed to a corresponding rail 12 and/or the upper surface 8 in two or more ways, such as, for example, by welding and by receiving a pin 17 through an aperture 26 in the stem 22. At least one staple 16 may be fabricated separately from a remainder of the cartridge 2, then affixed to the cartridge 2 as set forth above. Alternately, at least one staple 16 may be integral with a remainder of the cartridge 2.

The staples 16 may be arranged in the cartridge 2 in any suitable manner. As one example, one or more staples 16 may be arranged against a corresponding rail 12, with each stem 22 fixed to the corresponding rail 12. The staples 16 may be arranged relative to the rail 12 and to one another such that the tine 24 extending from a particular staple 16 is positioned on one lateral side of the rail 12, and the tine 24 extending from each longitudinally-adjacent staple 16 is positioned on the other lateral side of the rail 12. In this way, the tines 24 alternate sides relative to the rail 12 longitudinally along the rail 12, as seen most clearly in FIGS. 2-3. As another example, each staple 16 may include a single stem 22, with two tines 24 extending from it. Each tine 24 may extend from a lateral side opposed to the other. The stem 22 may be positioned on top of a rail 12, with each stem 22 fixed to the corresponding rail 12, and with each tine 24 positioned on a different lateral side of the corresponding rail 12. One tine 24 may be positioned longitudinally distal to the other tine 24 extending from the same stem 22. Such staples 16 may be arranged relative to the rail 12 such that the tines 24 alternate sides relative to the rail 12 longitudinally along the rail 12. As another example, at least one staple 16 is integral with the upper surface 8, and is affixed to a remainder of the upper surface 8 at the end 20 of the tine 24. In such a configuration, the staple 16 may be fabricated by punching, stamping, or otherwise dislodging it from the upper surface 8, such that the staple 16 extends from one end of a corresponding opening 10 in the upper surface 8, and the opening 10 results from the fabrication of the staple 16 associated with it. Further, in such a configuration, the stem 22 may be omitted from the staple 16. Regardless of the particular configuration of the staples 16, each tine 24 may be positioned adjacent to a corresponding opening 10 in the upper surface 8, and/or may be affixed to the upper surface 8 in proximity to the corresponding opening 10.

At least part of each staple 16 may be frangibly affixed to a remainder of the cartridge 2. "Frangibly affixed" is defined to mean that at least part of each staple 16 is fixed to a remainder of the cartridge 2 in such a manner that it must be sheared or otherwise broken off from a remainder of the cartridge 2 to be removed therefrom. As one example, at least one staple 16 may be frangible at the junction between the stem 22 and the tine 24. Such a junction may have a weakened area to facilitate frangibility. As another example, at least one staple 16 may remain intact during deployment, and the stem 22 of the staple 16 is frangible from the corresponding rail 12 and/or the upper surface 8. As another example, where the tine 24 is integral with the upper surface 8, the tine 24 may be frangible at the junction between the tine 24 and the upper surface 8.

The cartridge 2 may be actuated, and the staples 16 deployed, substantially as set forth in the Feeder Belt Document, with the following general differences. The wedge assembly 4 includes one or more wedges 30 configured generally as set forth in the Feeder Belt Document. Initially, the wedge or wedges 30 may be positioned proximal to the cartridge 2. In this way, the wedge or wedges 30 do not interfere with the insertion of the cartridge 2 into a remainder of the surgical stapler. The cartridge 2 may be inserted into the stapler, or may already be present in the stapler, prior to actuation of the stapler. The wedge assembly 4 is moved distally, advantageously by sliding. As the wedge assembly 4 moves distally, it slides the wedge or wedges 30 distally as well. Advantageously, one wedge 30 slides along a corresponding row of staples 16 to sequentially deform staples 16 outward through the corresponding openings 10 in the upper surface 8, and then break staples 16 from the cartridge 2. Such deformation and later breakage of the staple may be as set forth generally in the Feeder Belt Document. As one example, the stem 22 of one or more staples 16 is held substantially in place by its affixation to a corresponding rail 12 and/or to the upper surface 8, as set forth above. As a wedge 30 slides distally relative to the staple 16, the wedge 30 first engages the tine 24 of that staple 16, causing the tine 24 to move upward and to rotate about the junction between the tine 24 and the stem 22. Rotation of the tine 24 upward causes the tine 24 to move up through a corresponding opening 10 in the upper surface 8, through tissue, and then move into contact with an anvil (not shown), such as set forth in the Feeder Belt Document. Contact between the tine 24 and the anvil deforms the tine 24 to its closed configuration. As the wedge 30 continues to move distally relative to the staple 16, both the wedge 30 and the tine 24 may be shaped such that the wedge 30 may continue to contact and exert force on the tine 24 after the tine 24 has been deformed. This force increases until the tine 24 is broken, sheared or otherwise separated from the stem 22. As another example, this force increases until the stem 22 is broken, sheared or otherwise separated from a remainder of the cartridge 2, such as from a corresponding rail 12 and/or the upper surface 8 of the cartridge 2. The wedge 30 thereby may sequentially separate the frangible staples 16 from a remainder of the cartridge 2.

A knife 6 also may be connected to the wedge assembly 4, and may slide upward through the corresponding knife slot 32 in the upper surface 8 as the wedge assembly 4 moves distally through the cartridge 2. The knife 6 may be actuated, and may cut tissue, substantially as set forth in the Feeder Belt Document. Optionally, the knife 6 may be omitted from the wedge assembly 4, if desired. The knife 6 may be configured to move into the cartridge 2, then move upward through and out of the knife slot 32, then slide along the knife slot 32, then move downward through the knife slot 32. In this way, the knife 6 may be held in a position in which it does not extend through the knife slot 32 both before and after it has cut tissue, in order to enhance safety for the user and the patient.

After the wedge assembly 4 has been actuated to deploy one or more of the staples 16, the cartridge 2 is spent. The wedge assembly 4 then may be refracted proximally through and then out of the proximal end of the cartridge 2. The spent cartridge 2 then may be removed from a remainder of the surgical stapler. If desired, a new cartridge 2 may then be inserted into the surgical stapler in place of the previous, spent cartridge 2. The new cartridge 2 may be actuated substantially as described above.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical apparatus, comprising:
   a cartridge, comprising;
   at least one longitudinally-extending rail;
   an upper surface vertically spaced apart from said at least one rail; and
   multiple pins extending from said rail to said upper surface;
   multiple stems fixed to said cartridge rail and extending to said upper surface, wherein each of at least some of said stems includes an aperture extending from said rail to said upper surface, and wherein each of said pins extends through one of said apertures; and
   multiple surgical staples, each of said surgical staples comprising a single tine with a first end directly and frangibly affixed to only one of said stems and a second end that is free.

2. The surgical apparatus of claim 1, wherein each of said stems is substantially perpendicular to each of said tines.

3. The surgical apparatus of claim 1, wherein at least some of said stems are affixed to said upper surface and said rail.

4. The surgical apparatus of claim 1, wherein at least some of said stems are welded to at least one of said rails and also to said upper surface.

5. The surgical apparatus of claim 1, wherein at least one stem is fixed to a plurality of said staples.

6. The surgical apparatus of claim 1, wherein said upper surface further comprises a plurality of openings, wherein each said staple is affixed to said upper surface via one of said stems adjacent one of said openings.

7. The surgical apparatus of claim 6, wherein said stems are integral with said upper surface of said cartridge.

8. The surgical apparatus of claim 1, further comprising at least one wedge movable into said cartridge to deform and then shear at least one staple from said cartridge.

9. The surgical apparatus of claim 1, wherein each of said first ends of said tines is fixed to a first end of one of said pins.

10. The surgical apparatus of claim 9, wherein a second end of each of said pins is fixed to the upper surface.

11. The surgical apparatus of claim 1, wherein a first end of each of said pins is fixed to one of said rails, wherein a second end of each of said pins is fixed to the upper surface, and wherein at least some of the stems are affixed between one of said rails and said upper surface by one of the pins.

\* \* \* \* \*

UNITED STATES PATENT AND TRADEMARK OFFICE
CERTIFICATE OF CORRECTION

| | | |
|---|---|---|
| PATENT NO. | : 8,261,958 B1 | Page 1 of 1 |
| APPLICATION NO. | : 12/683382 | |
| DATED | : September 11, 2012 | |
| INVENTOR(S) | : Bryan D. Knodel | |

It is certified that error appears in the above-identified patent and that said Letters Patent is hereby corrected as shown below:

Col. 6, line 3, "cartridge" should be deleted.

Signed and Sealed this
Sixth Day of November, 2012

David J. Kappos
*Director of the United States Patent and Trademark Office*